(12) United States Patent
Hua

(10) Patent No.: US 12,414,786 B2
(45) Date of Patent: Sep. 16, 2025

(54) INTRAOPERATIVE IRRIGATION AND SUCTION

(71) Applicants: University of Iowa Research Foundation, Iowa City, IA (US); Duke University, Durham, NC (US)

(72) Inventor: Xiaoyang Hua, Iowa City, IA (US)

(73) Assignees: University of Iowa Research Foundation, Iowa City, IA (US); Duke University, Dunham (NC)

( * ) Notice: Subject to any disclaimer, the term of this patent is extended or adjusted under 35 U.S.C. 154(b) by 799 days.

(21) Appl. No.: 17/742,129

(22) Filed: May 11, 2022

(65) Prior Publication Data

US 2022/0361903 A1 Nov. 17, 2022

Related U.S. Application Data

(60) Provisional application No. 63/186,994, filed on May 11, 2021.

(51) Int. Cl.
*A61M 25/00* (2006.01)
*A61B 17/24* (2006.01)
*A61M 25/10* (2013.01)
*A61B 1/233* (2006.01)

(52) U.S. Cl.
CPC ............ *A61B 17/24* (2013.01); *A61M 25/10* (2013.01); *A61B 1/233* (2013.01); *A61B 2217/005* (2013.01); *A61M 2210/0681* (2013.01)

(58) Field of Classification Search
CPC . A61F 9/00736; A61M 1/774; A61M 3/0295; A61M 2025/0004; A61M 2025/0039; A61M 2025/1052; A61M 2025/1061; A61M 2210/0681; A61M 25/007; A61M 25/10; A61M 2202/0007; A61M 2202/0014; A61B 17/24; A61B 2217/005; A61B 2217/007
See application file for complete search history.

*Primary Examiner* — Deanna K Hall
(74) *Attorney, Agent, or Firm* — Dentons Davis Brown, P.C.; Matthew Warner-Blankenship; Kassandra Ricklefs

(57) ABSTRACT

A surgical system comprising a catheter comprising an irrigation tube, a suction tube, an occlusion balloon disposed about the irrigation tube and suction tube, and a console in operative communication with the irrigation tube and the suction tube. The surgical system also comprising a remote operations unit in communication with the console via a connector, wherein an input to the remote operations unit is communicated to the console, which in turn acts to operate the irrigation tube and suction tube in a manner corresponding to the input.

20 Claims, 11 Drawing Sheets

INTRAOPERATIVE IRRIGATION AND SUCTION

CROSS-REFERENCE TO RELATED APPLICATION(S)

This application claims the benefit under 35 U.S.C. § 119(e) to U.S. Provisional Application 63/186,994, filed May 11, 2021, and entitled "Intraoperative Irrigation and Suction System and Associated Devices and Methods," which is hereby incorporated herein by reference in its entirety for all purposes.

TECHNICAL FIELD

The disclosed technology relates generally to devices, systems, and methods for use in surgical applications such as sinus surgeries.

BACKGROUND

Currently, endoscopic sinus surgery is a leader in the global sinusitis treatment market and is expected to reach $50.41 billion by 2024. Yet, blood and space pose major challenges to efficient and safe endoscopic sinus surgery. The nasal cavity is a very narrow and vascularized space surrounded by vital structures including the orbit and its content laterally, the brain and skull base superiorly, and the carotid artery and optical nerves posterolaterally. Additionally, the mucosa that lines the nasal cavity is heavily vascularized and bleeds easily.

Currently, these challenges—blood and space—are dealt with by manually cleaning the lens of the surgical camera and use of suction to remove blood from the field via the nostril. This current practice requires transnasal insertion and removal of surgical tools into the nasal cavity multiple times throughout an operation. This type of procedure not only causes significant stress to the surgeon and prolongs the surgical and anesthesia time, but it also increases the risk of iatrogenic injuries to the fragile mucosa in the nasal cavity and the surrounding vital structures.

Thus, there is a need in the art for devices, systems, and methods for intraoperative irrigation and suction.

BRIEF SUMMARY

Discussed herein are various devices, systems, and methods relating to a catheter or device for use in intraoperative irrigation and suction for use in endoscopic sino-nasal and skull base surgery.

In Example 1, a surgical system comprising a catheter comprising an irrigation tube; a suction tube; an occlusion balloon disposed about the irrigation tube and suction tube; and a console in operative communication with the irrigation tube and the suction tube and a remote operations unit in communication with the console via a connector, wherein an input to the remote operations unit is communicated to the console, which in turn acts to operate the irrigation tube and suction tube in a manner corresponding to the input.

Example 2 relates to the surgical system of Example 1, further comprising a powered scope holder and a foot pedal configured to provide adjustments to scope holder and thereby a transnasally inserted endoscope.

Example 3 relates to the surgical system of any of Examples 1-2, wherein the irrigation tube is configured for single-direction irrigation via one or more side openings.

Example 4 relates to the surgical system of any of Examples 1-3, wherein the irrigation tube is configured for 360° irrigation via multiple side openings.

Example 5 relates to the surgical system of any of Examples 1-4, wherein the irrigation tube extends within a lumen of the suction tube.

Example 6 relates to the surgical system of any of Examples 1-5, further comprising a back flush port along the suction tube configured for cleaning of the suction tube intraoperatively.

Example 7 relates to the surgical system of any of Examples 1-6, wherein the remote operations unit comprises one or more foot pedals.

Example 8 relates to the surgical system of any of Examples 1-7, wherein the occlusion balloon is an eccentric balloon.

Example 9 relates to the surgical system of any of Examples 1-8, wherein the occlusion balloon is a concentric balloon.

Example 10 relates to the surgical system of any of Examples 1-9, further comprising an inflation port is communication with the occlusion balloon for the inflation and deflation of the occlusion balloon.

In Example 11, a catheter comprising a suction tube, an irrigation tube extending within a lumen of the suction tube, comprising one or more irrigation openings, a balloon disposed at a distal end of the suction tube, and an inflation port along the suction tube and in communication with the balloon for inflation of the balloon.

Example 12 relates to the catheter of Example 11, wherein the balloon, the suction tube, and the irrigation tube are concentric.

Example 13 relates to the catheter of any of Examples 11-12, wherein the one or more irrigation openings are configured for cleaning of a surgical camera lens and removal of blood from a surgical field.

Example 14 relates to the catheter of any of Examples 11-13, wherein the suction tube comprises a one directional valve at a distal end and a back flush port along the suction tube.

Example 15 relates to the catheter of any of Examples 11-14, wherein the catheter is configured for transoral insertion into a patient, such that the balloon is situated around the choana and nasopharynx.

Example 16 relates to the catheter of any of Examples 11-15, wherein the balloon prevents flow of fluids from nasal cavity to pharynx.

Example 17 relates to the catheter of any of Examples 11-16, further comprising an operations unit configured to control irrigation through the irrigation tube and suction through the suction tube.

Example 18 relates to the catheter of Example 17, wherein the operations unit comprises one or more foot pedals.

Example 19 relates to the catheter of any of Examples 17-18, wherein the operations unit is in communication with a console via a wired connection.

In Example 20, a surgical catheter comprising a suction tube comprising a back flush port and one-way valve, the suction tube configured to be in communication with a suction source, an irrigation tube extending within a lumen of the suction tube and extending distally past a distal end of the suction tube, the irrigation tube comprising a plurality of openings configured to irrigate a surgical cavity, a balloon disposed at the distal end of the suction tube, the balloon in communication with an inflation port, and a console for operation of the suction tube and irrigation tube, wherein the surgical catheter is configured to intraoperatively clean a surgical camera, surgical tools, and a surgical field.

While multiple embodiments are disclosed, still other embodiments of the disclosure will become apparent to those skilled in the art from the following detailed description, which shows and describes illustrative embodiments of the disclosed apparatus, systems and methods. As will be realized, the disclosed apparatus, systems and methods are capable of modifications in various obvious aspects, all without departing from the spirit and scope of the disclosure. Accordingly, the drawings and detailed description are to be regarded as illustrative in nature and not restrictive.

DETAILED DESCRIPTION

The various embodiments disclosed or contemplated herein relate to an irrigation and suction system and associated devices and methods of use. According to various implementations, the system allows for fluid-jet/water-jet, endoscopic, sino-nasal and skull base surgery. The system may provide controlled, adjustable, and/or an intermittent bolus or constant fluid flow through the nasal cavity, or other surgical field, during various procedures. This fluid flow may continuously or periodically remove blood and mucus in the nasal cavity, or other surgical field. The fluid flow may additionally remove blood, mucus, or other debris from the lens of an endoscope or other surgical camera to provide constant, clear visibility of the surgical field.

Various implementations of the system and devices may allow for dissection with both hands because the system can remove blood and clean the camera lens without removal of the endoscope, as is required by current methods and practice. The various implementations of the system allow for safer, more efficient, and more precise surgery.

Further, as would be understood, the flow of fluid through the surgical cavity may provide additional benefits in addition to cleaning the lens and removing fluids from the surgical field. For example, the fluid may act to cool the temperature of the lens or other surgical tool. Additionally, the system may allow for quick removal of aerosols generated intraoperatively, which may help protect medical professionals and patients from infections.

Figure 4:
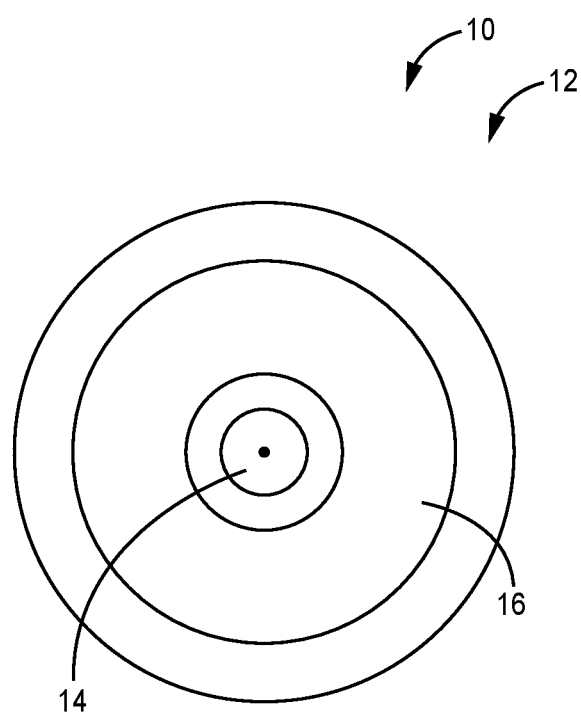
FIG. 4 is a cross sectional view of the catheter, according to one implementation.
Figure 5:
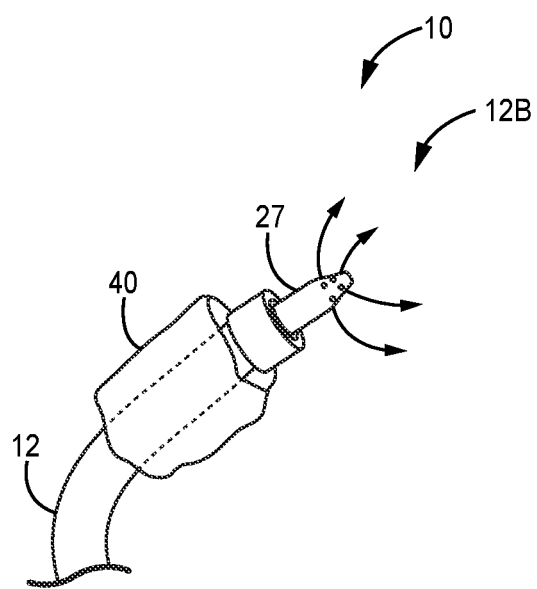
FIG. 5 is a side view of the distal end of the catheter, according to one implementation.

In further implementations, the catheter and system may be configured to allow insertion of another instrument through a center channel or suction tube (as seen for example in FIG. 2 at 16 and FIG. 4 at 16 as will be discussed further below). Such other instruments may include a flexible endoscope with irrigation and suctioning system, or other instruments as would be appreciated. In these and other implementations, it may not be needed to insert a scope transnasally and thus increasing space available for surgeons to place surgical tools via the nostrils. Additionally, using the herein described system the irrigations and cleansing system can be controlled away from the patient and therefor provide additional space in front of the nose/patient to perform a surgery/procedure with both hands.

While the various implementations discussed herein relate to surgery in the nasal cavity, it would be appreciated that the system may be adapted for use in alternative cavities, for example the system may be adapted for use in gastrointestinal endoscopy or other procedures as would be appreciated. Further adaptations may be made for use of the system for restoring nasal airflow or ventilating the nose by passively pulling the air through the nose.

Turning now to the figures, FIGS. 1-5 depict a nasal irrigation and suction system 10, according to various implementations. The system 10 comprises a generally elongate body 12 or catheter 12 comprising a one or more elongate tubes 14, 16. In these implementations, at least an irrigation tube 14 and a suction tube 16 are provided, though other configurations are of course possible.

Figure 1:
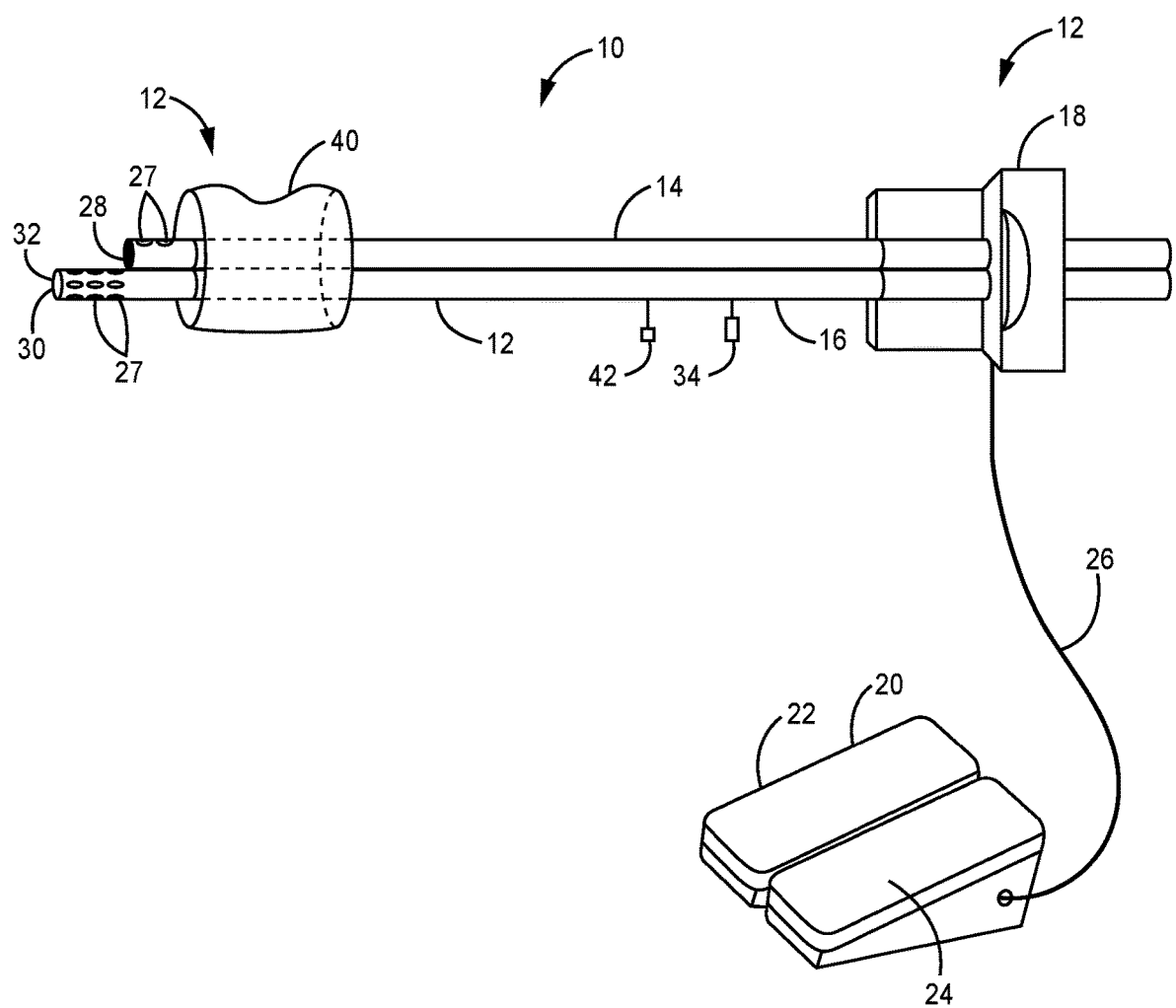
FIG. 1 shows the irrigation and suction system, according to one implementation.

In the implementation of FIG. 1, the irrigation tube 14 is an elongate tube defining a central lumen for the fluidic communication of a fluid, for example saline, into the surgical cavity. The suction tube 16 is configured for the application of suction to the surgical cavity, as would be understood. In the implementation of FIG. 1 the irrigation tube 14 and suction tube 16 are side-by-side or otherwise extending alongside each other. In alternative implementations, such as those shown in FIGS. 2-5, the irrigation tube 14 extends within the lumen of the suction tube 16. In these implementations the irrigation tube 14 and suction tube 6 are concentric (shown best in FIG. 4) but may be optionally eccentric or in any other configuration appreciated by those of skill in the art.

Figure 2:
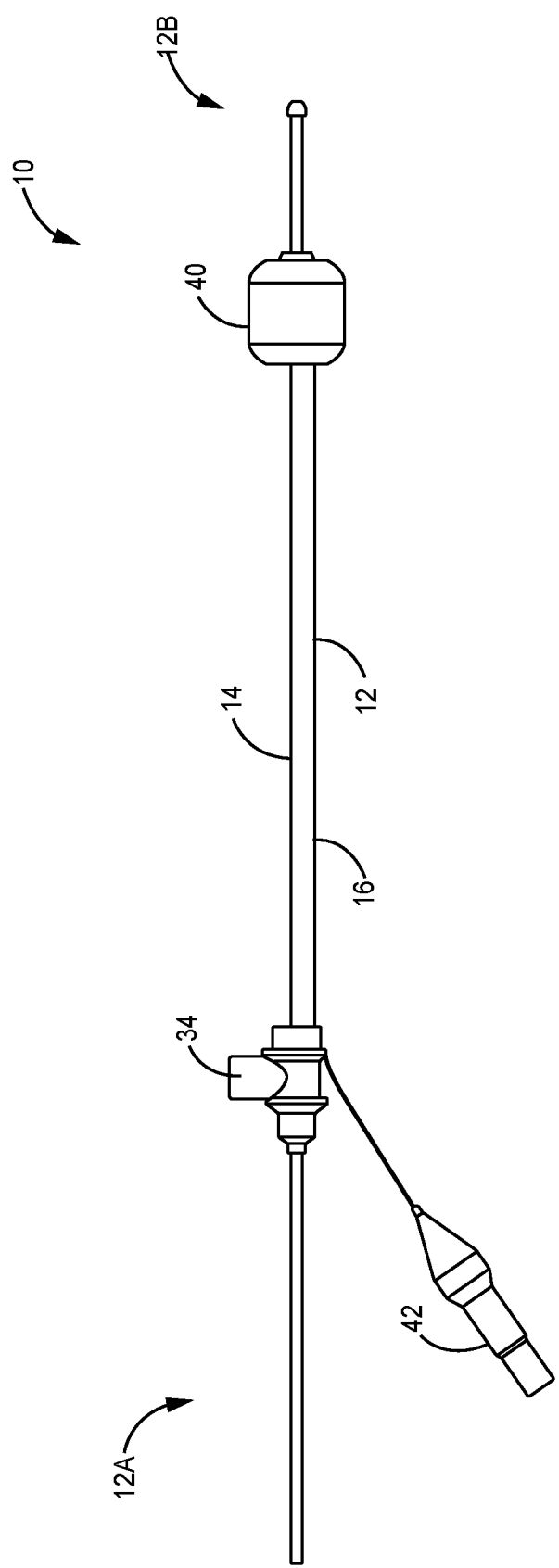
FIG. 2 is a side view of the irrigation and suction system, according to one implementation.
Figure 3:
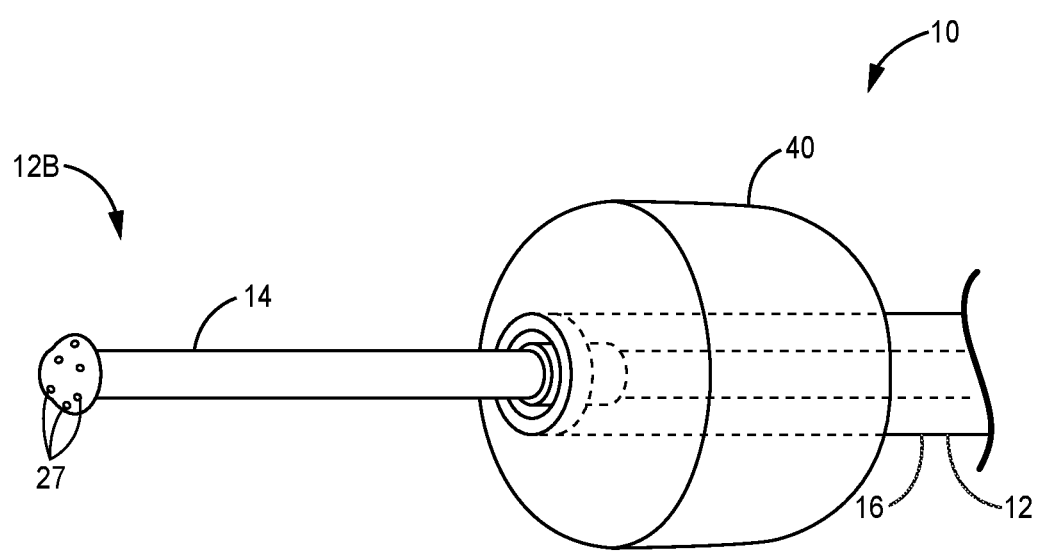
FIG. 3 is a perspective view of the distal end of the catheter, according to one implementation.

In certain implementations, such as that shown in FIG. 2, the center irrigation tubing 14 is adjustable in length and direction. That is, the irrigation tube 14 can be adjusted by a surgeon and/or other professional during a procedure by sliding the irrigation tubing 14 proximally or distally along the length of the suction tubing 16. To adjust the direction of the irrigator 14 (also referred to as the irrigation tube 14), the tip/distal end of the irrigator 14 can be adjusted trans-nasally by the surgeon to direct the irrigation to the area the surgeon is operating, such as in the nose, sinuses, along the skull base, or other area as would be understood.

Continuing with FIGS. 1-5, in certain implementations, the distal end 12B of the irrigation tube 14 of the catheter 12 has side pores 27 with an optionally blocked end 28. In this configuration, the irrigation fluids are directed superiorly to the lens and/or the area where dissection is performed. As such, in this configuration, the catheter 12 allows for the efficient cleaning of the lens and/or removal of the blood in the surgical field, while not allowing irrigation fluid discharge from the nostril where the fluid and other expelled liquids may contaminate the surgeon's face, the sterile field, or other items in the surgical theater. Further, the catheter 12 allows for cleansing a lens without the need to remove the endoscope for manual cleaning.

Both whole nose and/or targeted irrigation may be provided via the irrigation tube 14 or tubes 14. That is, the openings 27 (also referred to as side pores 27) may be in only one direction, or may be in multiple directions, or even allow for 360° or whole field irrigation. The pressure, flow rate, and trajectory of the various streams of irrigation fluid may be adjusted using different configurations of the tip of the irrigation tube 14, the sizes and locations of the pores 27, and pressure applied by the system 10.

In certain implementations, the distal end 12B of the suction tube 16 has both side pores 27 and an open end 30, as shown for example in FIG. 1. In certain implementations, the open end 30 includes a one-directional valve 32. In certain implementations, the suction tube 16 may not include side pores 27, such as when the irrigation tube 14 extends within the suction tube 16, but maintains an opening 30 at its end from which the irrigation tube 14 extends and where suction can be applied.

In various implementations, the catheter 12 includes a back flush port 34 along the suction tube 16. In these and other implementations, during the back flush process the one-directional valve 32 will open. In implementations, with a back flush system the back flush allows for cleaning of the suction tube 16 if it were to become clogged intraoperatively.

Continuing with the implementation of FIG. 1, the system 10 further comprises a console 18 disposed at the proximal end 12A of the catheter 12. In these implementations, the console 18 is configured to operate the various functions described herein, as well as be in communication with a remote operations unit 20, provided in certain implementations of the system 10. In certain implementations, the console 18 provides for powered irrigation and suction via the respective tubes 14, 16.

In the implementation of FIG. 1, the remote operations unit 20 is a foot operations unit 20 comprising an irrigation pedal 22 and a suction pedal 24. In these and other implementations, the remote operations unit 20 is configured to communicate the inputted actions of the operator to the console 18 via a connection 26. In various implementations, the connection 26 is a wired connection 26. It is readily appreciated that alternative communication systems can be used to provide the connection 26, such as any known wired or wireless communication system. It would be further appreciated that the remote operations unit 20 can take any number of forms understood in the art.

In various implementations, including those having a foot operations unit 20, the surgeon may control irrigation, suction, and therefore cleaning without having to remove surgical instruments from the surgical cavity. By minimizing the number of times items, such as the catheter 12, surgical tools, and/or the endoscope, must be inserted and removed from the nasal cavity or other surgical cavity the risk of iatrogenic trauma to the mucosa or other tissues is reduced while also increasing surgical efficiency and safety and reducing both the procedural and anesthesia time.

Continuing further with the implementation of FIGS. 1-5, the catheter 12 optionally further comprises a balloon 40 disposed at the distal end 12B of the catheter 12. The balloon 40 may prevent blood and other fluids from entering the nasopharynx, oropharynx, and airway minimizing the risk of intraoperative aspiration and post-operative hematemesis when used for nasal procedures. Further, the balloon 40 may lateralize the inferior turbinates during surgery, increasing the space for surgical instrumentation to be inserted transnasally.

In various implementations, the balloon 40 is an eccentric, off-centered, and/or "T" shaped balloon 40. In certain implementations, the balloon 40 is a low-pressure balloon and optionally high-volume. In various implementations, an inflation port 42 is provided along the catheter 12 to inflate to the balloon 40 after insertion of the catheter 12 into the nasal cavity, as would be appreciated. In alternative implementations, the balloon 40 may be concentric with the irrigation tube 14 and/or suction tube 16.

Turning now to FIGS. 6-11, in various implementations, the system 10 and more specifically the catheter 12, is inserted into the nasal cavity 1 transorally and placed around the choana (posterior nostril) and the nasopharynx.

Figure 6:
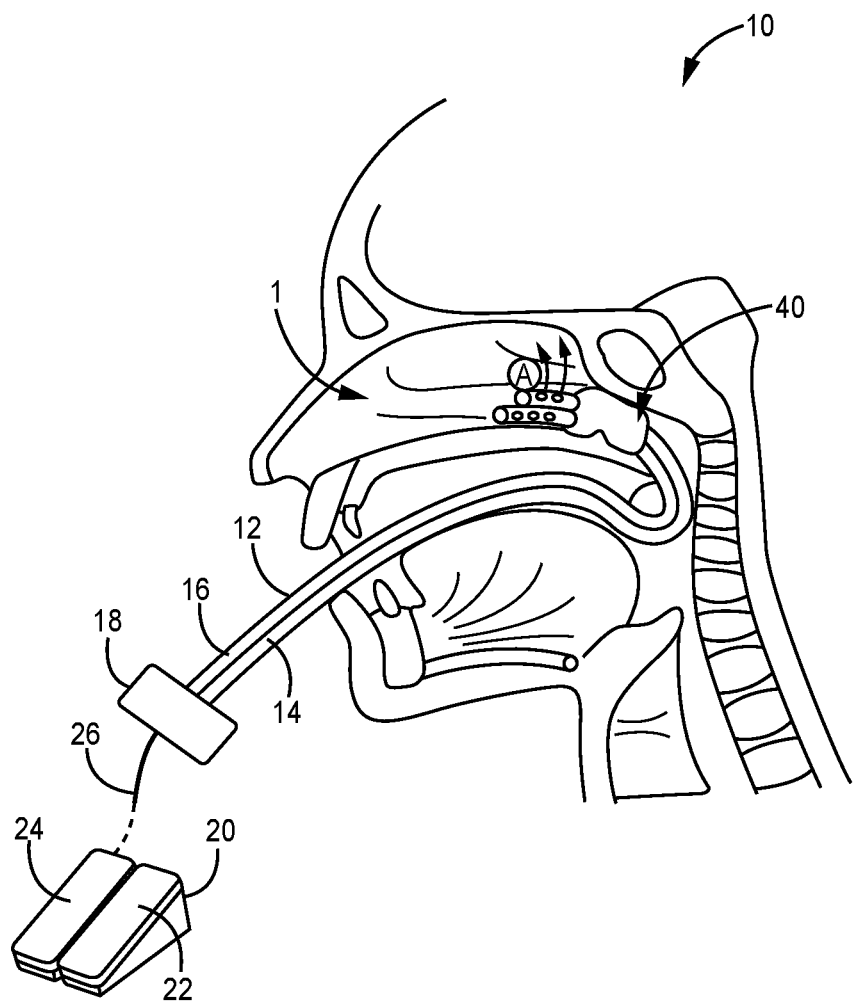
FIG. 6 is a side view of the irrigation and suction system in place within the nasal cavity, according to one implementation.
Figure 7:
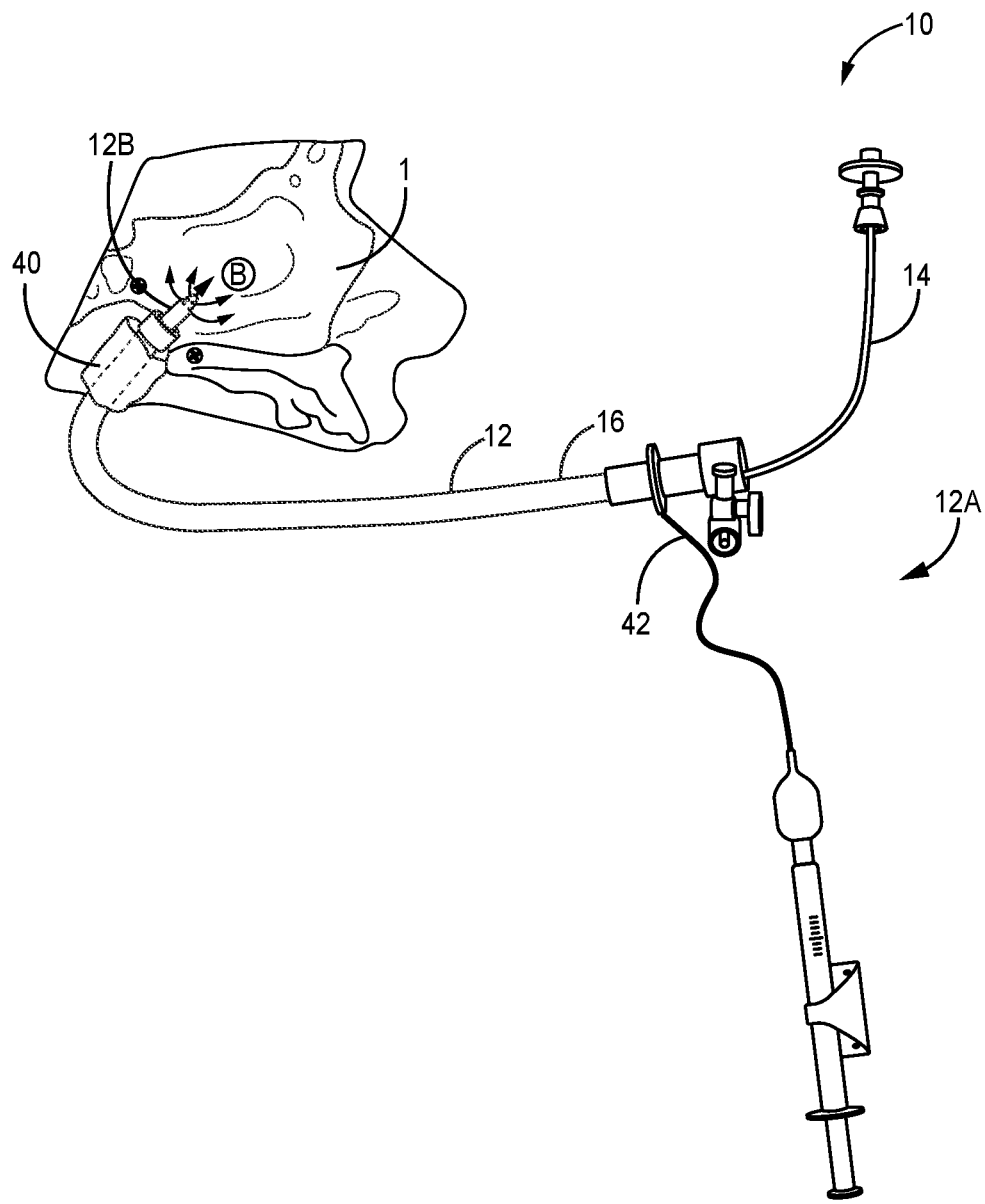
FIG. 7 is a side view of the system in place within a nasal cavity, according to one implementation.
Figure 8:
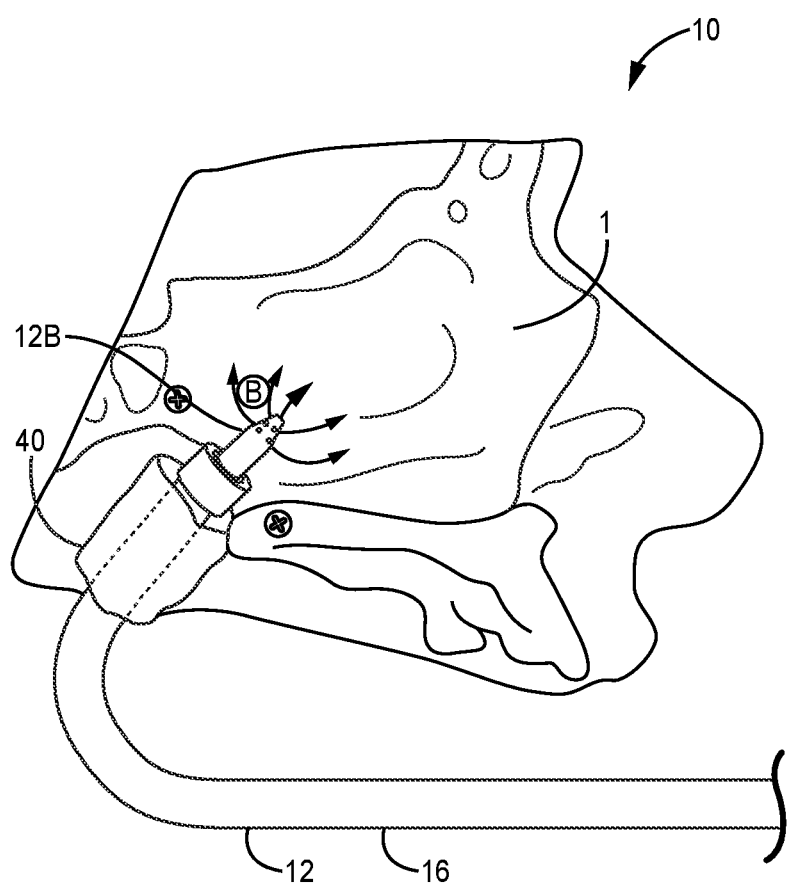
FIG. 8 is a side view of the catheter in place within a nasal cavity, according to one implementation.
Figure 9:
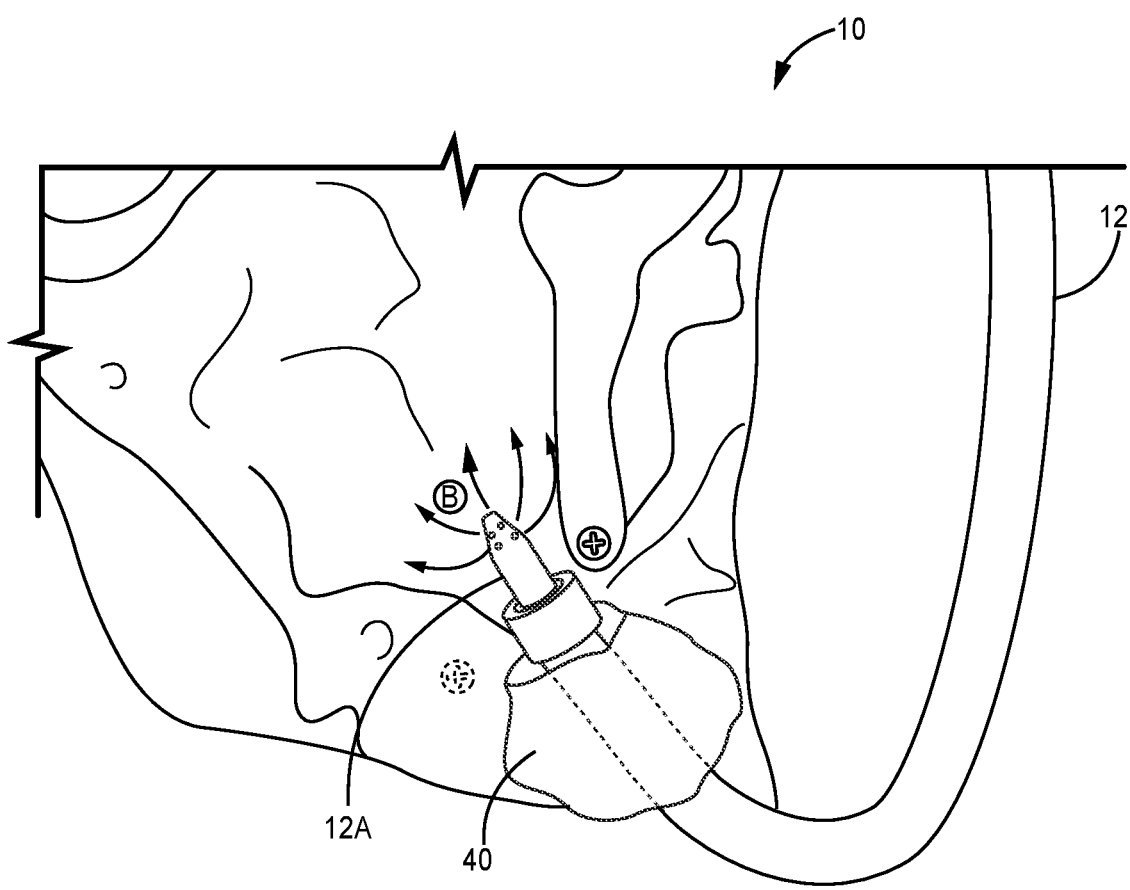
FIG. 9 is a side view of the distal end of the catheter in place within a nasal cavity, according to one implementation.

In various implementations, the off-centered balloon 40 will push the suction tube 16 to the floor of the nasal cavity after the balloon 40 is inflated, as shown for example in FIG. 6. These and other configurations may prevent accumulation of blood and fluids in the inferior meatus and nasal floor during a procedure.

Figure 10:
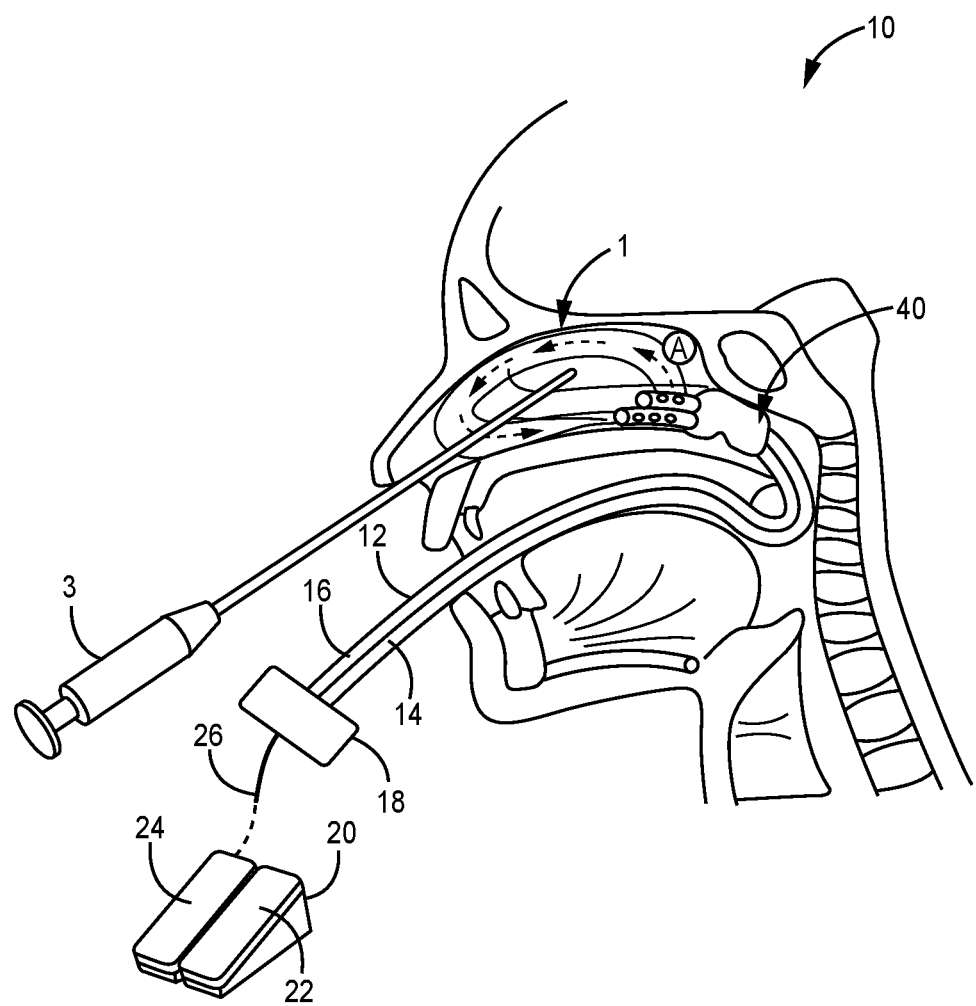
FIG. 10 is a side view of the irrigation and suction system in use, with a transnasally inserted and placed endoscope, according to one implementation.
Figure 11:
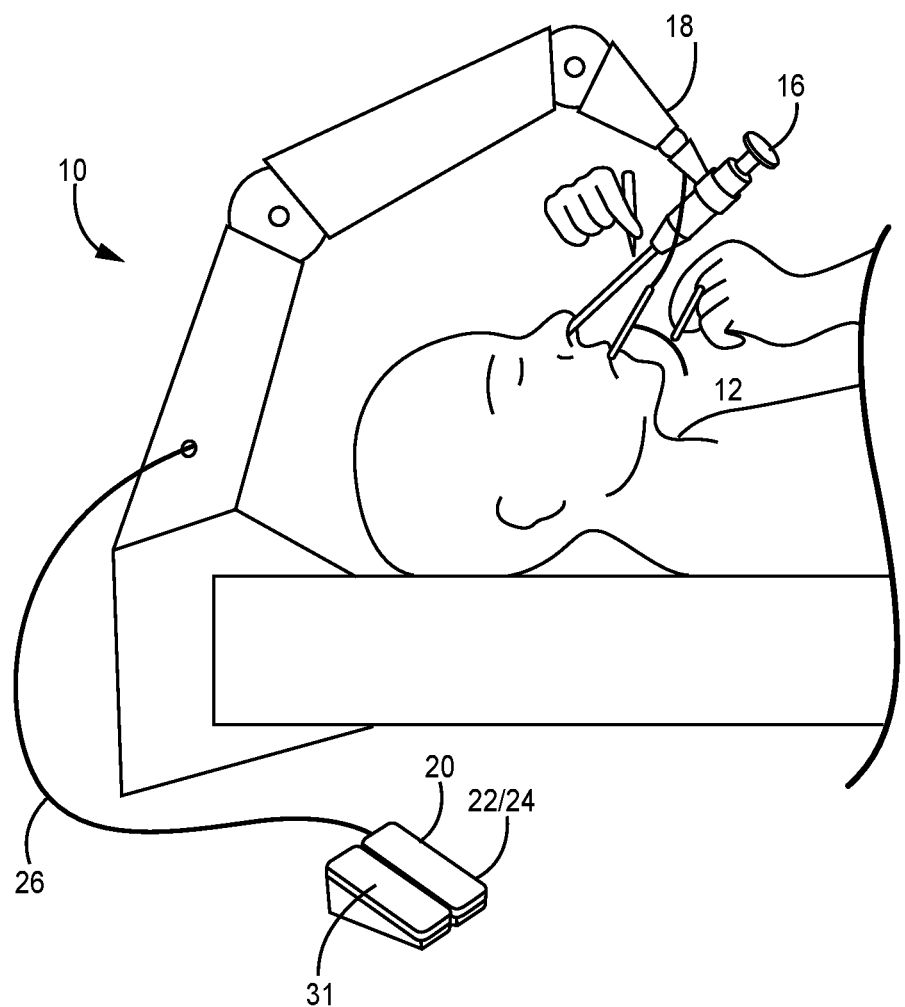
FIG. 11 is a side view of the system in use, according to one implementation.

In certain implementations, the balloon has an "T" shaped design or otherwise off-centered design to allow the balloon 40 to situate around the bony edge of the choana thus preventing the balloon 40 from sliding during a procedure, as would be understood. As noted above, the inflated balloon 40 blocks the choana which prevents blood and fluids from entering the pharynx thus minimizing the risk of intraoperative aspiration. The inflated balloon 40 will also push the inferior turbinate laterally thus increasing the dimensions of the nasal cavity. This will facilitate the placement of surgical instrument 3 and/or endoscope 3 transnasally (through the nostril), as shown in FIGS. 10-11.

In use, as shown in FIGS. 6-11, a fluid may enter the nasal cavity 1 via the irrigation tube 14, exiting the side pores 27, following the direction of arrows A or B. In various implementations, the irrigation fluid may be ejected superiorly and then encircle or otherwise flow through the nasal cavity clearing blood and/or mucus from the endoscope 3 or other surgical camera and ultimately being suctioned out of the cavity 1 via the suction tube 16, following the flow of arrow A, shown in FIGS. 6 and 10. Alternatively, the irrigation fluid may be ejected from all directions (360° irrigation) or multiple directions, causing a complete washing of the cavity, as shown for example in FIGS. 7-9.

In certain implementations, the fluid flow and suction may be constant or periodic. In various implementations, the surgeon may control the irrigation and suction via the remote operations unit 20, periodically releasing fluid and suctioning fluid.

As would be appreciated, the system 10 allows the surgeon to perform continuous transnasal dissection. Further, the transoral insertion of the catheter 12 allows for larger tubes 14, 16 compared to known transnasal catheters, as the anatomy of the choana is larger than that of the nostril, as would be appreciated. The larger tubes 14, 16 allow for more efficient removal of blood, mucus, and other fluids.

Turning now to FIG. 11, in various implementations, the endoscope 3 and/or the catheter 12 are supported by a scope holder 50. The scope holder 50 can support the endoscope 3 and/or catheter 12 to free the surgeon's hands such that the surgeon may have two free hands to dissect and perform other operations. In certain implementations, the scope holder 50 is mounted to the surgical table 5, as would be understood. In these and other implementations, the scope holder 50 may provide fine adjustments of the endoscope 3 in the nose. In various implementations, the scope holder 50 is powered and/or robotic and may be adjusted via a robotic system or a foot pedal 31, as would be appreciated by those of skill in the art. That is, in these implementations, a third pedal 31 on the operations unit 20 is used to control the powered scope holder 50, in addition to the pedals 22, 24 provided for the irrigation and suction system.

In further implementations, in use, the system 10 may be used with anterior nasal saline irrigation. Anterior saline irrigation through the nostrils, can optionally be administered by the scrub nurse or assistant, as would be understood. This may allow the surgeon to keep the endoscope and dissecting forceps in the nose during the anterior saline irrigation. The surgeon can then use the remote operations unit 20, such as foot pedal 24, to remove fluids using suction, as would be appreciated.

Although the disclosure has been described with reference to preferred embodiments, persons skilled in the art will recognize that changes may be made in form and detail without departing from the spirit and scope of the disclosed apparatus, systems and methods.

What is claimed is:

1. A surgical system comprising:
   (a) a catheter comprising:
      (i) an irrigation tube;
      (ii) a suction tube;
      (iii) an occlusion balloon disposed about the irrigation tube and suction tube; and
      (iv) a console in operative communication with the irrigation tube and the suction tube; and
   (b) a remote operations unit in communication with the console via a connector, wherein an input to the remote operations unit is communicated to the console, which in turn acts to operate the irrigation tube and suction tube in a manner corresponding to the input.

2. The surgical system of claim 1, further comprising a powered scope holder and a foot pedal configured to provide adjustments to the powered scope holder and thereby a transnasally inserted endoscope.

3. The surgical system of claim 1, wherein the irrigation tube is configured for single-direction irrigation via one or more side openings.

4. The surgical system of claim 1, wherein the irrigation tube is configured for 360° irrigation via multiple side openings.

5. The surgical system of claim 1, wherein the irrigation tube extends within a lumen of the suction tube.

6. The surgical system of claim 1, further comprising a back flush port along the suction tube configured for cleaning of the suction tube intraoperatively.

7. The surgical system of claim 1, wherein the remote operations unit comprises one or more foot pedals.

8. The surgical system of claim 1, wherein the occlusion balloon is an eccentric balloon.

9. The surgical system of claim 1, wherein the occlusion balloon is a concentric balloon.

10. The surgical system of claim 1, further comprising an inflation port is communication with the occlusion balloon for inflation and deflation of the occlusion balloon.

11. A catheter comprising:
    (a) a suction tube;
    (b) an irrigation tube extending within a lumen of the suction tube, comprising one or more irrigation openings;
    (c) a balloon disposed at a distal end of the suction tube; and
    (d) an inflation port along the suction tube and in communication with the balloon for inflation of the balloon.

12. The catheter of claim 11, wherein the balloon, the suction tube, and the irrigation tube are concentric.

13. The catheter of claim 11, wherein the one or more irrigation openings are configured for cleaning of a surgical camera lens and removal of blood from a surgical field.

14. The catheter of claim 11, wherein the suction tube comprises a one directional valve at a distal end and a back flush port along the suction tube.

15. The catheter of claim 11, wherein the catheter is configured for transoral insertion into a patient, such that the balloon is situated around choana and nasopharynx.

16. The catheter of claim 12, wherein the balloon prevents flow of fluids from nasal cavity to pharynx.

17. The catheter of claim 11, further comprising an operations unit configured to control irrigation through the irrigation tube and suction through the suction tube.

18. The catheter of claim 17, wherein the operations unit comprises one or more foot pedals.

19. The catheter of claim 17, wherein the operations unit is in communication with a console via a wired connection.

20. A surgical catheter comprising:
    (a) a suction tube comprising a back flush port and one-way valve, the suction tube configured to be in communication with a suction source;
    (b) an irrigation tube extending within a lumen of the suction tube and extending distally past a distal end of the suction tube, the irrigation tube comprising a plurality of openings configured to irrigate a surgical cavity;
    (c) a balloon disposed at the distal end of the suction tube, the balloon in communication with an inflation port; and
    (d) a console for operation of the suction tube and irrigation tube,
    wherein the surgical catheter is configured to intraoperatively clean a surgical camera, surgical tools, and a surgical field.

* * * * *